United States Patent [19]

Ruminski et al.

[11] Patent Number: 4,747,871

[45] Date of Patent: May 31, 1988

[54] 2,6-BIS(TRIFLUOROMETHYL)-3-HYDROXYCARBONYL PYRIDINE, SALTS AND GAMETOCIDES

[75] Inventors: Peter G. Ruminski, Fenton; Om P. Dhingra, Chesterfield, both of Mo.

[73] Assignee: Monsanto Company, St. Louis, Mo.

[21] Appl. No.: 930

[22] Filed: Jan. 7, 1987

[51] Int. Cl.$^4$ .................... A01N 43/40; C07D 213/80
[52] U.S. Cl. .......................................... 71/94; 546/318
[58] Field of Search ............................. 546/318; 71/94

[56] References Cited

U.S. PATENT DOCUMENTS 4,692,184  9/1987  Lee ....................................... 546/318

Primary Examiner—Richard A. Schwartz
Assistant Examiner—Dale A. Bjorkman
Attorney, Agent, or Firm—Robert B. Martin

[57] ABSTRACT

The present invention relates to pyridines of the formula

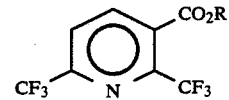

wherein R is selected from the group consisting of hydrogen and agriculturally acceptable cations, and their use as gametocides.

8 Claims, No Drawings

2,6-BIS(TRIFLUOROMETHYL)-3-HYDROXYCARBONYL PYRIDINE, SALTS AND GAMETOCIDES

FIELD OF THE INVENTION

The present invention relates to certain substituted pyridines and their use as gametocides.

BACKGROUND OF THE INVENTION

An effective gametocide is a chemical compound that, when applied to a plant during sexual development, is capable of sterilizing a plant's male gametes while leaving the plant's female gametes, or at least a significant proportion of them, capable of undergoing cross fertilization with subsequent high yields of fertile, viable hybrid seed.

The utility of a gametocide lies in the area of plant hybridization. By causing pollination of one variety of a plant species by a different variety of the same species, a hybrid plant is obtained. By careful selection of the parents, hybrids can be obtained with specific combinations of desirable traits such as plant size, grain yield, disease resistance, herbicide tolerance and climatic adaptation.

Hybridization utilizing cytoplasmic male sterility is available and is used to produce commercial hybrid corn and wheat seed. However, using such techniques, it can take years to develop lines to the point that commercial quantities of hybrid seed are produced. The use of an effective gametocide significantly reduces this development time.

Some plants, such as corn, can be easily hybridized without resort to the use of gametocides because the organ containing the male gametes are exposed and can easily be removed. This leaves the female gametes available for cross-fertilization.

However, this is not true with plants which are self-pollinating by nature such as wheat. The male and female wheat gametes are found inside the same flower which remains closed until the male anthers release their pollen onto the female gametes to fertilize them. Thus, when the flower opens, fertilization is normally complete. For a gametocide to be useful on wheat it must sterilize the male gametes and avoid interfering with the opening of the flower when the female gametes are ready for fertilization.

Substituted pyridones and pyridazines are known in the art as gametocides as disclosed in U.S. Pat. Nos. 4,115,101 and 4,345,934.

However, there still is a need in the art for a more effective gametocide which effectively sterilizes the male gametes while leaving the female gametes capable of undergoing cross fertilization with a subsequent high yield of fertile viable hybrid seed.

SUMMARY OF THE INVENTION

The present invention relates to certain substituted pyridines and the use of these pyridines as gametocides. The pyridines of the present invention have the following formula:

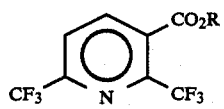

wherein R is selected from the group consisting of hydrogen and agriculturally acceptable cations.

The process of the present invention involves selectively sterilizing the male gametes of a plant by applying to a plant a compound selected from the group consisting of 2,6-bis(trifluoromethyl)-3-hydroxycarbonyl pyridine and agronomically acceptable salts thereof.

The process of the present invention can be utilized in the production of hybrid plants including monocotyledons such as wheat. A more thorough disclosure of the present invention is presented in the detailed description which follows.

DETAILED DESCRIPTION

The present invention relates to certain substituted pyridines and the use of these pyridines as gametocides. The pyridines of the present invention have the following formula:

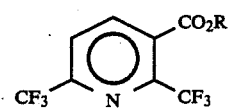

wherein R is selected from the group consisting of hydrogen and agriculturally acceptable cations.

The term "agriculturally acceptable cations" is understood to mean those cations that are commonly used to form the salt. Such cations include, but are not limited to, alkali metal, alkaline earth, substituted amine and ammonium cations. The agriculturally acceptable cations will not have any ecologically unacceptable consequences for the plant, the soil or the general environment. Those skilled in the art will be able to readily identify other suitable agriculturally acceptable cations.

The process of the present invention involves selectively sterilizing the male gametes of a plant by applying to a plant a compound selected from the group consisting of 2,6-bis(trifluoromethyl)-3-hydroxycarbonyl pyridine and an agronomically acceptable salt thereof.

The use of a salt in the process of the present invention is preferred since such salts are generally more water-soluble than the corresponding pyridine. This makes application of the compound significantly easier in practice.

The Route A below schematically depicts a method whereby the substituted pyridine compounds of this invention may be prepared from compounds which are known in the art. In this route, acetone dicarboxylic acid 1 is cyclized into the corresponding anhydride 2 by reacting it with acetic anhydride. The anhydride 2 is dissolved in methanol and stirred to form the acetone dicarboxylic acid monomethyl ester 3. The monomethyl ester is then reacted with isobutylene in acid and a suitable organic solvent to form t-butyl, methyl acetone dicarboxylate 4. The dicarboxylate 4 is then sequentially reacted with magnesium chloride in a suitable organic solvent and with trifluoroacetic anhydride to form methyl, t-butyl diesterpyrone 5. The pyrone 5 is then reacted with trifluoroacetic acid to form the acid methyl ester pyrone 6. The pyrone 6 is then refluxed in a suitable organic solvent to remove the acid moiety and form the methyl ester pyrone 7. The pyrone 7 is then aminated by addition of methanol and ammonia to form 2,6-bis(trifluoromethyl)-3-methoxycarbonyl-4-hydroxy pyridine 8. Pyridine 8 is then chlorinated with a suitable chlorinating agent such as POCl$_3$ to form 2,6-bis(trifluoromethyl)-3-methoxycarbonyl-4-chloropyridine 9. Pyridine 9 is then hydrogenated using standard laboratory techniques to form 2,6-bis(trifluoromethyl)-3-methoxycarbonyl pyridine 10. The pyridine 10 is then hydrolyzed with a strong base to form 2,6-bis(trifluoromethyl)-3-hydroxycarbonyl pyridine 11.

The enamine 2 so produced is then reacted with 2–2.5 equivalents of a strong base, suitably lithium diisopropylamide to generate in situ a dianion which is then reacted with an ester of trifluoromethyl carboxylic acid. The reaction product is a mixture of a substituted 4-hydroxy-2,6-bis-(trifluoromethyl)-3-(methoxycarbonyl)pyridine and a substituted 2,3-dihydro-2-hydroxy-4-pyridone, which dehydrates readily when heated to form a 4-hydroxy-2,6-bis-(trifluoromethyl)-3-(methoxycarbonyl)pyridine 3. The pyridine 3 is then chlorinated with a suitable chlorinating agent such as POCl₃ to form 2,6-bis(trifluoromethyl)-3-methoxycarbonyl-4-chloropyridine 4. Pyridine 4 is then hydrogenated using standard laboratory techniques to form 2,6-bis(trifluoromethyl)-3-methoxycarbonyl pyridine 5. The pyridine 5 is then hydrolyzed with a strong base to form 2,6-bis(trifluoromethyl)-3-hydroxycarbonyl pyridine 6.

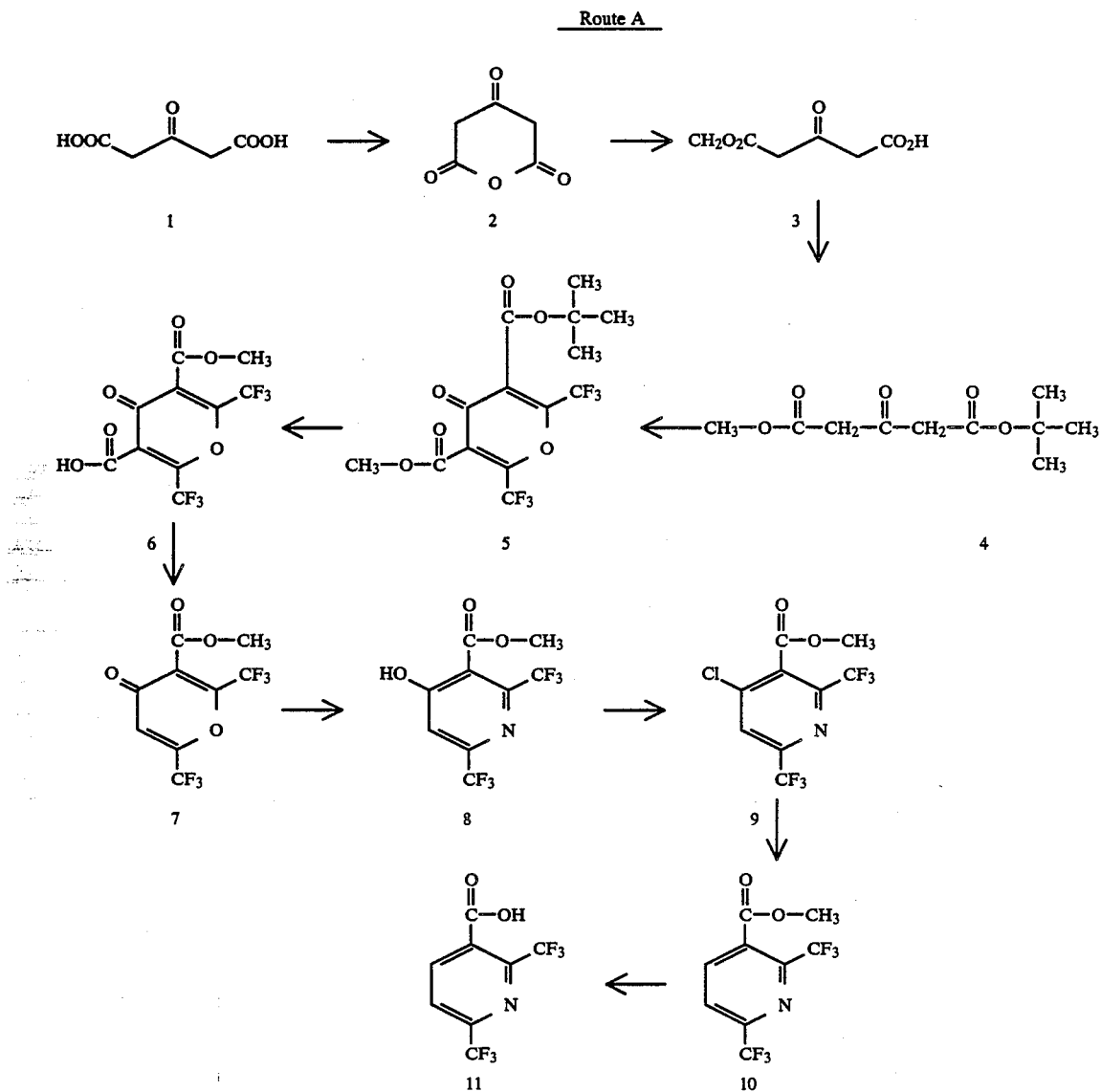

Route A

An alternative method of making intermediates to compounds used in the process of the present invention is disclosed in EPO application No. 85870152.7 published Nov. 5, 1985 and is shown in Route B below.

In Route B, a 3-ketoester 1 of the formula shown is reacted with trifluoroacetonitrile in the presence of a base. Examples of suitable bases are potassium t-butoxide, sodium in dimethoxyethane, sodium acetate, and the like. The result of this reaction is a 2-alkanoyl-3-amino-2-alkenoate ester 2; i.e., an enamine compound.

Route B

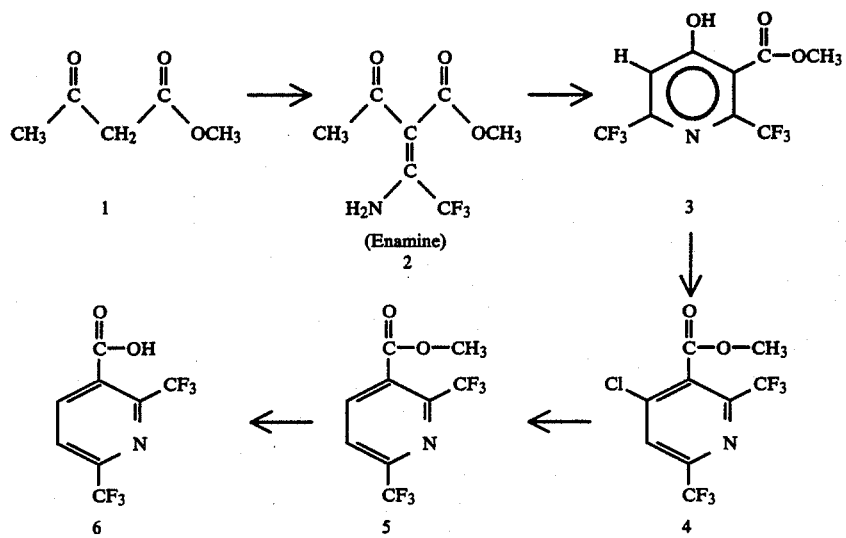

The salts useful in the practice of the present invention may be made by reacting the corresponding pyridine 6 with the appropriate base in a suitable organic solvent.

The following Examples 1-9 are detailed descriptions of the methods of preparing compounds useful in the practice of the present invention. These detailed descriptions fall within the scope of and serve to exemplify the more generally described method above. These Examples are presented for illustrative purposes only and are not intended as a restriction on the scope of the invention. All parts by weight unless otherwise indicated.

EXAMPLE 1

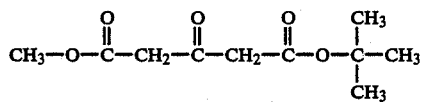

3-oxo-1,1-dimethylethyl, methyl ester pentanedioic acid

To acetic anhydride (350 ml) at 0° acetone dicarboxylic acid (200 g, 1.37 mole) was added slowly over ½ hour with vigorous stirring. After stirring 3 hours, a white solid was filtered and washed with ether (100 ml). Drying the solid 3 hours at 50° C. (0.1 mm) gave acetone dicarboxylic acid anhydride (149 g), m.p. 134°-136° C.

The acetone dicarboxylic acid anhydride (20 g) just prepared was dissolved in methanol (80 ml) causing an exotherm. After stirring 1½ hours, contents were concentrated in vacuo and the residue was dried under high vacuum to give a light brown oil: acetone dicarboxylic acid, monomethyl ester (24.0 g).

The acetone dicarboxylic acid, monomethyl ester (24.0 g) just prepared was mixed with ether (20 ml), conc $H_2SO_4$ (1 ml) and condensed isobutylene (35 g) in a 500 ml pressure bottle. Contents were stoppered and shaken mechanically on a Parr hydrogenation apparatus for 20 hours. After releasing the excess isobutylene, the contents were diluted with ether (150 ml) and washed with water (2×25 ml), sat'd aqueous $NaHCO_3$ (4×25 ml), water (2×25 ml) and brine (1×50 ml). The ether layer was dried over $Na_2SO_4$ and concentrated in vacuo leaving an amber oil. Distillation at 103°-105° C. (2.6 mm) gave a colorless oil, 21.1 g (63%).

Elemental analysis for $C_{10}H_{16}O_5$

|  | C | H |
|---|---|---|
| Calculated | 55.55 | 7.46 |
| Found | 55.58 | 7.46 |

EXAMPLE 2

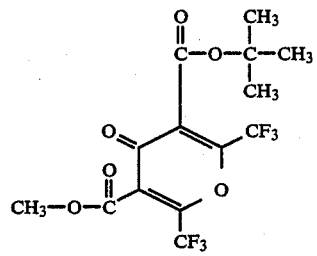

2H-pyran-3,5-dicarboxylic acid, 2,6-bis(trifluoromethyl)-3-methyl-5-(1,1-dimethylethyl)ester The pentanedioic acid from Example 1 (10.8 g. 0.05 mole), anhydrous magnesium chloride (4.8 g 0.05 mole) and pyridine (8 ml) were mixed in anhydrous THF (15 ml) and refluxed for one hour. After cooling contents to −5° C., trifluoroacetic anhydride (28.3 ml, 0.2 mole) was added dropwise over 15 minutes, keeping the temperature less than 0°. Stirred for one hour at 0°-5° and then contents were concentrated in vacuo. The residue (oily solid) was taken up in $CH_2Cl_2$ and washed with water (2×500 ml), dried over $MgSO_4$ and concentrated in vacuo, to give a light yellow solid (16.8 g). The solid was twice recrystallized from cyclohexane to give a white solid, 8.8 g (49%): m.p. 114°-117° C.

Elemental analysis for $C_{14}H_{12}F_6O_6$

|  | C | H |
|---|---|---|
| Calculated | 43.09 | 3.10 |
| Found | 43.09 | 3.05 |

EXAMPLE 3

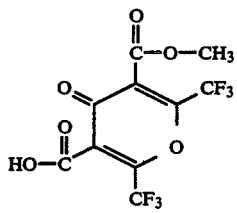

2H-pyran-3,5-dicarboxylic Acid,
4-Oxo-2,6-bis(trifluoromethyl)-3-methyl ester

The ester from Example 2 (21.1 g, 0.054 mole) and trifluoroacetic acid (25 ml) were stirred magnetically for 2 hours. Contents were concentrated in vacuo and the residue left under high vacuum to remove the last traces of trifluoroacetic acid. $CH_2Cl_2$ was added to the residue and a solid was filtered. Recrystallization from toluene gave a white solid 14.0 g (78%): m.p. 160°–163° C.

Elemental analysis for $C_{10}H_4F_6O_6$

|  | C | H |
|---|---|---|
| Calculated | 35.47 | 1.34 |
| Found | 35.50 | 1.30 |

EXAMPLE 4

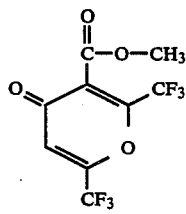

4H-pyran-3-carboxylic acid,
4-oxo-2,6-bis(trifluoromethyl), methyl ester

The ester from Example 3 (5 g, 0.015 mole) was refluxed in xylene (100 ml) for 3 hours. After cooling, contents were concentrated in vacuo and the residue, a light amber oil, was purified by kugelrohr distillation at 50° (0.15 mm) to give a white solid, 3.5 g (80%): m.p. 36°–38° C.

Elemental analysis for $C_9H_4F_6O_4$

|  | C | H |
|---|---|---|
| Calculated | 37.26 | 1.39 |
| Found | 37.25 | 1.48 |

EXAMPLE 5

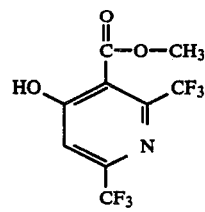

2,6-bis(trifluoromethyl)-3-methoxy carbonyl-4-hydroxy pyridine

To the ester of Example 4 (28.5 g, 0.1 mole) was added a solution of methanol containing anhydrous ammonia (approximately 100 ml), causing an exotherm and immediate dissolution. After stirring for 0.5 hours, contents were concentrated in vacuo. The residue was dissolved in water (200 ml) and extracted with ether. The water layer was made acidic to pH 7.0 with 2N HCl, and again extracted with ether. The water layer was made more acidic to pH 2.0 and extracted with ether. This last ether extraction was dried over $MgSO_4$ and concentrated in vacuo leaving a solid (25.3 g). The solid was recrystallized from hexane to yield 24.0 g (83%) of the product as a white solid m.p. 62°–75° C.

Elemental analysis for $C_9H_5F_6NO_3$

|  | C | H |
|---|---|---|
| Calculated | 37.38 | 1.74 |
| Found | 37.35 | 1.74 |

EXAMPLE 6

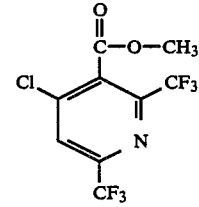

2,6-bis(trifluoromethyl)-3-methoxycarbonyl-4-chloropyridine

A mixture of 6.7 g (0.0232 mol) of product of Example 5, 2.8 g (0.026 mol) of 2,6-lutidine, and 50 ml of $POCl_3$ was held at reflux for 18 hours and concentrated. The residue was treated with water and extracted with ether. The ether extract was washed with 10% NaOH and then with saturated NaCl, dried, and concentrated. The residue was Kugelrohr distilled at pot temperature 90° C. The distillate was recrystallized from hexane at low temperature to give 1.4 g (19.7%) of product. M.P. 48°–49° C.

Elemental analysis for $C_9H_4Cl_1F_6NO_2$

|  | C | H |
|---|---|---|
| Calculated | 35.14 | 4.56 |
| Found | 35.20 | 4.55 |

EXAMPLE 7

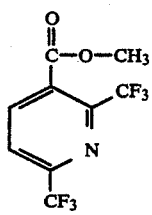

2,6-bis(trifluoromethyl)-3-methoxycarbonyl pyridine 20 g (0.065 mole) of the product of Example 6 in 100 ml of methanol was hydrogenated for 2 days at room temperature and at 50 p.s.i. in the presence of 2 g of 10% Pd/C. The catalyst was filtered off and the solvent from the filtrate was removed under vacuum. The residue was taken up in ethyl ether, washed with H$_2$O, 2X with sat. NaHCO$_3$, 2X with H$_2$O and dried over MgSO$_4$. The ether was removed under vacuum and the residue was purified by HPLC (15% Et. Acet./Hexane) to yield 11.3 g (64%) of a clear liquid.

Elemental analysis for C$_9$H$_5$F$_6$NO$_2$

|  | C | H |
|---|---|---|
| Calculated | 39.58 | 1.85 |
| Found | 40.03 | 1.87 |

EXAMPLE 8

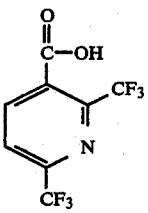

2,6-bis(trifluoromethyl)-3-hydroxycarbonyl pyridine 7 g (0.026 mole) of the product of Example 7, 5 g of potassium hydroxide, 10 ml of H$_2$O and 35 ml ethanol were stirred overnight at reflux. The solvent was then removed under vacuum. H$_2$O was added to the residue. This aqueous layer was extracted 2X with ether (ether layer discarded). The aqueous layer was then acidified with conc. HCl. The product was extracted with ether. The ether layer was washed 2X with H$_2$O and dried over MgSO$_4$. The ether was then removed under vacuum and the resulting solid was dried to yield 6.07 g (91%) of a white solid. M.P. 102°–104° C.

Elemental analysis for C$_8$H$_3$F$_6$NO$_2$

|  | C | H |
|---|---|---|
| Calculated | 37.08 | 1.17 |
| Found | 37.08 | 1.17 |

EXAMPLE 9

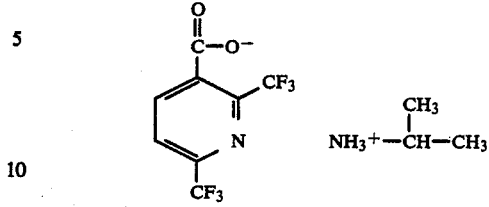

Isopropylamine salt of 2,6-bis(trifluoromethyl)-3-hydroxycarbonyl pyridine

To 1.7 g (0.0066 mole) of the product of Example 8 dissolved in 25 ml of ethyl ether is added 0.4 g (0.0066 mole) of isopropylamine in 5 ml of ethyl ether dropwise and at room temperature. This was stirred overnight at room temperature. A precipitate formed after 15 min. The precipitate was filtered, washed with ether and dried under vacuum to yield 1.78 g (85%) of a white solid. M.P. 135–137.

Elemental analysis for C$_{11}$H$_{12}$F$_6$N$_2$O$_2$

|  | C | H |
|---|---|---|
| Calculated | 41.52 | 3.80 |
| Found | 41.69 | 3.83 |

In the process of the present invention a sterilizing effective amount of the gametocide should preferably be applied after initiation of sexual development (e.g. spike formation), but prior to sexual maturity, that is before pollen is shed from the anthers. Generally, application in wheat should occur when the spike or head length is from about 1 to 9 cm, preferably about 4 to 7 cm and most preferably about 5 cm. In other plants application should preferably be when the plants have reached a corresponding degree of sexual maturity. It has been found that application of the compound early in the day generally results in both greater gametocide activity and plant injury.

In the process of the present invention the gametocide sterilizes most male gametes while leaving a significant portion of the female gametes capable of fertilization. Further, the gametocide has a minimum effect on the rest of the plant (e.g. stunting, chlorosis etc.).

In the process of the present invention, the gametocide is applied at the appropriate time at a rate of about 1 to about 20 lbs/a preferably about 7 to about 12 lbs/a. It will be obvious to those skilled in the art that the optimum application rate for the gametocide will depend on a variety of factors such as plant type, soil type, fertility, environmental factors and the like and those skilled in the art will be capable of readily determining the optimum based on the Examples herein and their experience. Spray volumes may be varied substantially e.g., from 30 gal/ac to 300 gal/a without any appreciable effect on activity of the compounds.

In the process of the present invention, the compound is applied at the appropriate time to the plant locus. Application to the plant locus include application to the foliage and to the plant growth medium e.g., soil to enable assimilation of the chemical into the growing plant. The compounds in the process of the present invention can be used with adjuvants in liquid or solid form. The compositions are prepared by admixing the compounds with an adjuvant including diluents, extenders, carriers, and conditioning agents to provide compositions in the form of finely-divided particulate solids, granules, pellets, solutions, dispersions, or emulsions. Thus, they can be used with an adjuvant, such as a finely-divided solid, a liquid of organic origin, water, a wetting agent, binder, carrier, or any suitable combination of these.

The compounds can also be used in the form of liquids and wettable powders. These preferably contain as a conditioning agent one or more surface-active agents in amounts sufficient to render a given compound readily dispersible in water or in oil. The incorporation of a surface-active agent into the compound can enhance its efficacy. By the term "surface-active agent" it is understood that wetting agents, dispersing agents, suspending agents, and emulsifying agents are included therein. Anionic, cationic, and nonionic agents can be used.

It is believed that suitable wetting agents are alkyl benzene and alkyl naphthalene sulfonates, sulfonated fatty alcohols, amines or acid amides, long chain acid esters of sodium isothionate, esters of sodium sulfosuccinate, sulfated or sulfonated fatty acid esters, petroleum sulfonates, sulfonated vegetable oils, ditertiary acetylenic glycols, polyoxyethylene derivatives of alkylphenyls (particularly isooctylphenol and nonylphenol) and polyoxyethylene derivatives of the mono-higher fatty acid esters of hexitol anhydrides (e.g., sorbitan). Preferred surfactants are dihexyl ester of sodium sulfosuccinic acid, POE 20 sorbitan monolaurate and octylphenoxy polyethoxy ethanol.

Wettable powders or dispersable granules are water-dispersible compositions containing one or more active ingredients, an inert solid extender, and one or more wetting and dispersing agents. The inert solid extenders are usually of mineral origin, such as the natural clays, diatomaceous earth, salts and synthetic minerals, derived from silica and the like. Examples of such extenders include kaolinites, attapulgite clay, salts and synthetic magnesium silicate.

Aqueous suspensions or emulsions may be prepared by stirring an aqueous mixture of a water-insoluble active ingredient and an emulsification agent until uniform and then homogenized or milled to give stable emulsion or suspension of very finely-divided particles. The resulting concentrated aqueous suspension is characterized by its extremely small particle size, so that when diluted and sprayed, coverage is very uniform.

Concentrates are usually solutions of the active ingredients in water-immiscible or partially water-immiscible solvents together with a surface active agent. Suitable solvents for the active ingredients of this invention will be known to those skilled in the art.

Granules are physically stable particulate compositions comprising the active ingredients adhering to or distributed through a basic matrix of an inert, particulate extender. In order to aid leaching of the active ingredient from the particulate, a surface active agent, such as those listed hereinbefore, can be present in the composition. Natural clays, pyrophyllites, illite, gypsum, and vermiculite are examples of operable classes of particulate mineral extenders. The preferred extenders are the porous absorptive, preformed particles, such as preformed and screened particulate attapulgite or heat-expanded, particulate vermiculite, and the finely-divided clays, such as kaolin clays, hydrated attapulgite, or bentonitic clays. These extenders are sprayed or blended with the active ingredient to form the herbicidal granules.

In order to avoid the time consuming effort of field testing a very large number of chemical compounds as potential gametocides, the art skilled have developed various bioactivity screens to identify chemical compounds which may exhibit gametocide activity.

A primary screen for wheat involves applying a chemical compound to a plant in a growth chamber at the appropriate time when the spike length is about 5 cm, and observing the effect on the plant. Potential gametocide activity is evidenced by the flower opening wide which normally only occurs after the pollen from the male gamete has been discharged onto the female gamete. This is known as showing "open head morphology". Further, the compound should show only a slight stunting of the plant.

Chemical compounds which show suitable open head morphology in the primary screen are then tested in a secondary screen. The secondary screen generally involves applying the chemical compound to the wheat plant when the spike has reached the appropriate length and then bagging a portion of the plant heads. When seeds are large enough to be seen, the spikes are evaluates for the number of seed set. The following examples are illustrative.

EXAMPLE 35

The process of the present invention is illustrated by testing the gametocides of Examples 8 and 9 utilizing the following general procedure. Awned hard red spring wheat cultivar Anza was grown in a growth chamber set at low humidity (70%), at 19° C.:17° C. (day:night) temperatures with a 16 hour photoperiod, and at a light intensity of 800 $\mu$E. Seven seeds per six inch pot were planted in a soilless medium of Metro-Mix200 supplemented with 93 g Osmocote (14-14-14) Controlled Release Fertilizer, 93 g Peters (14-7-7) Slow Release Fertilizer, 17 g Micromax Micronutrients per cubic foot of Metro-Mix200. Approximately 10–14 days after planting, pots were thinned to six plants per pot. Chemical treatments were foliar applied using an enclosed track sprayer chamber. This consists of a compressed air reservoir equipped with a manual speed adjustment and a field sprayer nozzle. This method simulated actual field spraying techniques. The test consisted of using three rates on one date in a carrier solution of 50% Acetone-50% $H_2O$-0.2%Tween20 sprayed at a rate equivalent to 300 gal/acre. On the spray date the mean spike length of primary tillers averaged about 4.82 cm. Controls treated with carrier solution were included for comparison. After spike emergence and before anthesis, glassine bags were placed over approximately 12–15 heads per pot to prohibit all but self-pollination. When seeds were large enough to be easily seen (approximately 4 weeks after heading), bagged spikes were evaluated for the number of seed set. The data is the average of two or more replicas. In all of the tests the controls were all fertile.

| Example No. | Spray Rates (lb/a) | | |
|---|---|---|---|
| | 3.1 | 9.3 | 15.5 |
| | (means % of sterility) | | |
| 8 | 50 | 99 | 99 |
| 9 | 14 | 88 | 97 |

We claim:

1. A compound of the formula

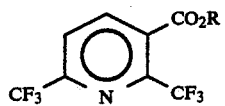

wherein R is selected from the group consisting of hydrogen and agriculturally acceptable cations.

2. A process for selectively sterilizing the male gametes of a plant which comprises applying to a plant locus a compound selected from the group consisting of 2,6-bis(trifluoromethyl)-3-hydroxycarbonyl pyridine and agronomically acceptable salts thereof.

3. The process of claim 2 wherein said salt is the diisopropylamine salt.

4. The process of claim 2 wherein said salt is the sodium salt.

5. The process of claim 2 wherein the compound is applied to the plant locus at a time after initiation of sexual development but before sexual maturity.

6. The process of claim 2 wherein the plant is a monocotyledon.

7. The process of claim 2 wherein the plant is wheat.

8. The process of claim 2 wherein the compound is applied to the plant locus at a rate of about 1 to about 20 lb/a.

* * * * *